United States Patent
Piccirilli et al.

(10) Patent No.: US 7,371,420 B2
(45) Date of Patent: *May 13, 2008

(54) METHOD FOR PRODUCING AN AVOCADO UNSAPONIFIABLE RICH IN FURAN LIPIDS

(75) Inventors: Antoine Piccirilli, Versailles (FR); Jacques Legrand, Neuilly sur Eure (FR)

(73) Assignee: Laboratoires Expanscience, Courbevoie (FR)

( * ) Notice: Subject to any disclaimer, the term of this patent is extended or adjusted under 35 U.S.C. 154(b) by 130 days.

This patent is subject to a terminal disclaimer.

(21) Appl. No.: 10/522,907

(22) PCT Filed: Jul. 28, 2003

(86) PCT No.: PCT/FR03/02379

§ 371 (c)(1),
(2), (4) Date: Oct. 3, 2005

(87) PCT Pub. No.: WO2004/012496

PCT Pub. Date: Feb. 12, 2004

(65) Prior Publication Data

US 2006/0099323 A1 May 11, 2006

Related U.S. Application Data

(63) Continuation of application No. 10/206,792, filed on Jul. 29, 2002, now Pat. No. 6,994,875.

(30) Foreign Application Priority Data

Jul. 29, 2002 (WO) .................... PCT/FR02/02715

(51) Int. Cl.
*A61K 35/78* (2006.01)

(52) U.S. Cl. ..................... 424/777; 424/769

(58) Field of Classification Search ............ None
See application file for complete search history.

(56) References Cited

U.S. PATENT DOCUMENTS

| 4,560,568 A | | 12/1985 | Curiel |
| 5,262,163 A | * | 11/1993 | Rancurel .................... 424/769 |
| 6,994,875 B2 | * | 2/2006 | Piccirilli et al. ............ 424/777 |

FOREIGN PATENT DOCUMENTS

| FR | 2 653 974 A | 5/1991 |
| FR | 2 678 614 A | 1/1993 |
| FR | 2 678 632 A | 1/1993 |
| FR | 2 798 667 A | 3/2001 |

OTHER PUBLICATIONS

Faines, E., , et al., "Influence of Avocado Oil Processing on the Nature of Some Unsaponifiable Constituents", Journal of the American Oil Chemists' Society, American Oil Chemists' Society Campaign, vol. 72, No. 4, pp. 473-476 (1995).

Rancurel, A: "L' avocet: Son huile et son insaponifiable. Utilisation cosmétique", Parfums, Cosmetiques, Aromes, Societe D'Expansion Technique et Economique, S.A., vol. 61, pp. 91-95 (1985).

* cited by examiner

*Primary Examiner*—Susan Coe Hoffman
(74) *Attorney, Agent, or Firm*—Foley & Lardner LLP

(57) ABSTRACT

The present invention relates to a process for obtaining a furan lipid-rich unsaponifiable material from avocado, which comprises the successive steps (1) of controlled dehydration of fresh avocados or of avocados that have undergone preliminary transformations, (2) of extraction of the oil from dehydrated fruit, (3) of a heat treatment of the extracted oil and of a step of concentration of the unsaponifiable fraction of the oil or alternately, these two operations possibly being carried out successively in this order or in the reverse order, and finally (4) a step of saponification and of extraction of the unsaponifiable material.

13 Claims, No Drawings

METHOD FOR PRODUCING AN AVOCADO UNSAPONIFIABLE RICH IN FURAN LIPIDS

This application is a national stage entry of PCT/FR03/02379, filed Jul. 28, 2003, which is a continuation of U.S. patent application Ser. No. 10/206,792, filed Jul. 29, 2002, now U.S. Pat. No. 6,994,875.

The present invention relates to a process for obtaining a furan lipid-rich unsaponifiable material from avocado.

Avocado comprises, in a known manner, particular lipids of furan type, the main component of which is a linoleic furan:

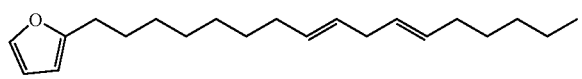

Thus, according to the invention, the expression "furan lipids from avocado" means components corresponding to the formula:

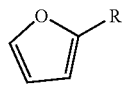

in which R is a $C_{11}$-$C_{19}$ and preferably $C_{13}$-$C_{17}$ linear hydrocarbon chain that is saturated or comprising one or more ethylenic or acetylenic unsaturations. These furan lipids from avocado have been described especially in Farines, M. et al, 1995, *J. of Am. Oil Chem. Soc.* 72, 473.

The unsaponifiable material is the fraction of a fatty substance which, after prolonged action of an alkaline base, remains insoluble in water and may be extracted with an organic solvent. Five major groups of substances are present in most of the unsaponifiable materials of plant oils: saturated or unsaturated hydrocarbons, aliphatic or terpenic alcohols, sterols, tocopherols, carotenoid pigments and xanthophylls.

Patent FR 91 08301 describes a process for obtaining an unsaponifiable material from avocado starting with an avocado oil enriched in one of its fractions, known as fraction H, which in fact corresponds to these same furan lipids. The preparation of such an unsaponifiable material that is rich in furan lipids, the content of which can range from 30 to 60%, is essentially conditioned by a controlled heating of the fresh fruit, sliced beforehand into thin slices, at a temperature of between 80 and 120° C., and for a duration preferably chosen between 24 and 48 hours. In this process, the heat treatment may be preceded by dehydration of the fruit, but, preferably, it is performed concomitantly with drying of the fruit. This heat treatment allows, after extraction, the production of a furan lipid-rich avocado oil. Finally, using this oil, the unsaponifiable fraction is obtained according to a standard saponification process, completed by step of liquid-liquid extraction.

A first drawback of this process is the need to heat to a relatively high temperature, at least equal to 80° C., for relatively long periods, 1 to 2 days, slices of fruit rich in lipids that are readily oxidizable under these conditions. In addition, this type of heat treatment brings about, in plant-based food matter, secondary degradation reactions that are well known to those skilled in the art, such as the Maillard reactions, which cause unwanted browning of the products, and the appearance of flavours and aromas that are often unpleasant.

Moreover, this type of heat treatment, carried out in air, without preliminary establishment of an inert atmosphere, may be accompanied by major chemical changes, especially in the presence of heat-sensitive substrates such as lipids (e.g. unsaturated fatty acids) and their unsaponifiable fraction (e.g. vitamin E). Thus, the heat processes will favour the heat-oxidation of the substrates, free-radical reactions responsible for the appearance of peroxides, and also intramolecular or intermolecular condensation reactions that are the cause of the formation of heavy products.

In fact, the conjunction of these uncontrolled secondary processes may lead to a major impairment of the organoleptic properties of the treated products and to a profound change in their physicochemical properties. Finally, this type of product may be the cause of a drastic reduction in the yield of target product, in this instance furan lipids, and may thus be harmful to the overall economic viability of the process.

Given the therapeutic value of the furan lipid-rich unsaponifiable material from avocado for its beneficial and curative action on connective tissue, especially in inflammatory pathologies such as osteoarthritis, periodontitis and scleroderma, and its generally high cost, there is thus strong interest in preparing, in the best possible yield, unsaponifiable fractions from avocado oil that are rich in furan lipids and very poor in oxidation and condensation compounds.

The Applicant has thus developed a process for obtaining in high yield an unsaponifiable material from avocado that is rich in furan lipids, i.e. with a content ranging from 50% to 80%, and that has low contents of heavy products and peroxides.

This process comprises the following successive steps:
(1) a step of controlled dehydration of fresh avocados or of avocados that have undergone preliminary transformations, performed at a temperature of between −50° C. and 75° C.,
(2) a step of extraction of the oil from the dehydrated fruit,
(3) a step, alternatively,
   a. of heat treatment of the extracted oil at a temperature that can range from 80 to 150° C., optionally under an inert atmosphere, and then a step of concentration of the unsaponifiable fraction of the oil, or
   b. of a step of concentration of the unsaponifiable fraction of the oil, followed by a heat treatment at a temperature that can range from 80 to 150° C., optionally under an inert atmosphere, followed by
(4) a step of saponification and extraction of the unsaponifiable material.

The expression "avocado that has undergone preliminary transformations" means the co-products derived from the processes of extraction of the fresh avocado oils, especially those derived from the "centrifugation" processes. Thus, in terms of "avocado that has undergone preliminary transformations", mention may be made especially of i) avocado milks 5 (semi-liquid puree) obtained by pressing the pulp, or ii) the products of clearing of the partially de-oiled pulp by centrifugation, by-products generally present at the outlet of the centrifuge sieves, or the centrifugation pellets produced during the separation.

Other sources of avocado that come under the expression "avocado that has undergone preliminary transformations" may also be mentioned. Thus, avocado cakes, co-produced during the cold-pressing of the fruit (fresh or dried) or liquid-solid extraction of avocado oil from fresh or dried fruit, using an organic solvent, may also constitute, in this form, an alternative starting material that may be used in the context of the present invention.

Finally, although poor in oil, avocado kernels may potentially constitute a source of lipids and may be used in the context of the present invention.

The term "dehydration", performed in step (1) of the process, more generally means all of the techniques known to those skilled in the art which allow the water to be removed from a compound. Among these techniques that may be mentioned are drying under a stream of hot air or under a controlled atmosphere (e.g. nitrogen), at atmospheric pressure or under vacuum, in a thick layer or a thin layer, and also microwave drying, spray-drying, freeze-drying and osmotic dehydration in solution (direct osmosis) or in solid phase (e.g. drying in osmosis bags). In the context of the present process, for reasons of ease of industrial implementation and for reasons of cost, drying in ventilated dryers, in a thin layer and under a stream of hot air, at a temperature of between 70 and 75° C. for 8 to 36 hours, is preferred.

The extraction step (2) may be carried out by any means known to those skilled in the art, preferably by a simple cold-pressing or by means of a solvent at low temperature.

According to the process of the invention, the heat treatment step carried out in step (3) a. or b. may be performed in the presence or absence of an acid catalyst. The term "acid catalysts" means, in the broad sense, homogeneous mineral and organic catalysts, such as hydrochloric acid, sulphuric acid, acetic acid or para-toluenesulphonic acid, but also, and preferably, heterogeneous solid catalysts such as silica, alumina, silica-aluminas, zirconias, zeolites and acidic resins. Acidic aluminas with large specific surface areas, i.e. at least equal to 200 $m^2/g$, will be chosen in particular. Catalysts of acidic alumina type are preferred for carrying out the process of the invention. Advantageously, this heat treatment is carried out under a continuous stream of nitrogen. Preferably, the heat treatment temperature is between 80 and 130° C.

The concentration step in step (3)a. or (3)b. may be a cold crystallization or a molecular distillation.

The molecular distillation may be performed at a temperature of between 180 and 260° C. while maintaining a pressure of between $10^{-3}$ and $10^{-2}$ mmHg. This step of molecular distillation of the unsaponifiable material is preferably performed using a device chosen from molecular distillation devices of centrifugal type and molecular devices of wiped-film type. Molecular distillation devices of centrifugal type are known to those skilled in the art. For example, patent application EP 493 144 describes a molecular distillation device of this type. In general, the product to be distilled is spread in a thin layer over the heated surface (hot surface) of a conical rotor rotating at high speed. The distillation chamber is placed under vacuum. Under these conditions, evaporation takes place rather than boiling, from the hot surface, of the constituents of the unsaponifiable material, the advantage being that the oil and the unsaponifiable material (these products being notoriously fragile) are not degraded during the evaporation. Molecular distillation devices of wiped-film type, which are also known to those skilled in the art, comprise a distillation chamber equipped with a rotating doctor blade, allowing the product to be distilled to be spread continuously over the evaporation surface (hot surface). The product vapours are condensed by means of a cold finger placed in the centre of the distillation chamber. The peripheral feed and vacuum systems are very similar to those of a centrifugal distillation device (feed pumps, vane vacuum pumps and oil diffusion pumps, etc.). The residues and distillates are recovered in glass flasks by gravitational flow.

Step (4) of saponification of the oil or of the oily extract may be carried out in the presence of potassium hydroxide or sodium hydroxide in alcoholic medium, preferably ethanolic medium, followed by one or more extraction(s). Extraction with a suitable organic solvent (liquid-liquid extraction) in-order to separate the fatty acid soaps and the unsaponifiable compounds, is particularly suitable for use. The appropriate organic solvent may be chosen, for example, from the group of alkanes, haloalkanes, aromatic solvents, ethers such as methyl tert-butyl ether (MTBE) and ethyl ether, or any other suitable solvent that is immiscible with the aqueous-alcoholic solution.

A haloalkane will preferably be chosen, in particular 1,-2-dichloroethane.

The extraction solution obtained is then preferably centrifuged, filtered and then washed with water to remove the residual traces of alkalinity. Finally, the extraction solvent is evaporated thoroughly to recover the unsaponifiable material. Needless to say, it is also possible to include additional operations known to those skilled in the art, such as a deodorization step.

The following non-limiting examples illustrate the invention.

Starting with the same batch of fresh avocados, with a net weight of 1000 kg, of the Fuerte variety from South Africa, 6 sub-batches of 50 kg each are made.

EXAMPLE 1

Process of Vigorous Heat Treatment of the Fruit 50 kg of fresh avocados are cut into thin slices 2 to 5 mm thick, including the kernel, using a disc slicer. The drying device is a temperature-regulated oven with a stream of hot air. The sliced avocados are spread to a thickness of 4 to 5 cm on staged trays. The drying temperature is set at 85° C. and its duration is 48 hours. Once dried, the fruit is ground and then subjected to a cold pressing. This operation is performed on a small laboratory Komet press. The extracted oil is then filtered through a Büchner funnel, and then stored under nitrogen protected from light and moisture.

The oil obtained is then distilled in a Leybold KDL 4 wiped-film molecular distillation device, at a temperature of 230° C. and under a vacuum of $10^{-3}$ mmHg. The yield of distillate for this operation is 9.2%.

The distillate obtained is saponified for 4 hours at reflux, in the presence of 175 g of 50% potassium hydroxide and 875 g of ethanol, in a glass reactor equipped with a mechanical stirrer and on which is mounted a condenser. At the end of the reaction, the mixture is cooled to 30° C. and then diluted by adding demineralized water. The aqueous-alcoholic solution (AAS) obtained is then extracted with 1,2-dichloroethane using a separating funnel.

The organic phases are then combined and dried over anhydrous sodium sulphate. The dissolved unsaponifiable fraction is finally recovered after evaporating off the solvent and drying under vacuum. This step is carried out in a rotary evaporator, at 70° C., under a vacuum of 1 mmHg for 2 hours. 126 g of unsaponifiable fraction from avocado are thus recovered, and are then stored under nitrogen while awaiting analysis.

The physicochemical and chromatographic analysis of this fraction gave the following results:

peroxide value: 87.2 meq $O_2/kg$ saponification number: 12.3 mg KOH/g
incineration residue: 0.3%
furan lipid content: 49.2%
fatty alcohol content: 14.7
heavy compounds: 22.3%

EXAMPLE 2

Process for the Vigorous Heat Treatment of the Oil 50 kg of fresh avocados are cut into thin slices 2 to 5 mm thick, including the kernel, using a disc slicer. The drying device is a temperature-regulated oven with a stream of hot air. The sliced avocados are spread to a thickness of 4 to 5 cm onto staged trays. The drying temperature is set at 70° C. and its duration is 48 hours. Once dried, the fruit is ground and then subjected to a cold pressing. This operation is performed on a small laboratory Komet press. The extracted oil is then filtered through a Büchner funnel, and then stored under nitrogen protected from light and moisture.

This oil is then heated at 85° C. for 48 hours, under a continuous stream of nitrogen, in a glass reactor equipped with a mechanical stirrer.

The oil obtained is then distilled in a Leybold KDL 4 wiped-film molecular distillation device, at a temperature of 230° C. and under a vacuum of $10^{-3}$ mmHg. The yield of distillate for this operation is 9.4%.

350 g of this distillate are saponified for 4 hours at reflux, in the presence of 175 g of 50% potassium hydroxide and 875 g of ethanol, in a glass reactor equipped with a mechanical stirrer and on which is mounted a condenser. At the end of the reaction, the mixture is cooled to 30° C. and then diluted by adding demineralized water. The aqueous-alcoholic solution (AAS) obtained is then extracted with 1,2-dichloroethane using a separating funnel.

The organic phases are then combined and dried over anhydrous sodium sulphate. The dissolved unsaponifiable fraction is finally recovered after evaporating off the solvent and drying under vacuum. This step is carried out in a rotary evaporator, at 70° C., under a vacuum of 1 mmHg for 2 hours. 141 g of unsaponifiable fraction from avocado are thus recovered, and are then stored under nitrogen while awaiting analysis.

The physicochemical and chromatographic analysis of this fraction gave the following results:
peroxide value: 23.2 meq $O_2$/kg
saponification number: 11.3 mg KOH/g
incineration residue: 0.2%
furan lipid content: 57.6%
fatty alcohol content: 13.7
heavy compounds: 14.3%

EXAMPLE 3

Process for the Vigorous Heat Treatment of the Distillate 50 kg of fresh avocados are cut into thin slices 2 to 5 mm thick, including the kernel, using a disc slicer. The drying device is a temperature-regulated oven with a stream of hot air. The sliced avocados are spread to a thickness of 4 to 5 cm onto staged trays. The drying temperature is set at 70° C. and its duration is 48 hours. Once dried, the fruit is ground and then subjected to a cold pressing. This operation is performed on a small laboratory Komet press. The extracted oil is then filtered through a Büchner funnel, and then stored under nitrogen protected from light and moisture.

The oil obtained is then distilled in a Leybold KDL 4 wiped-film molecular distillation device, at a temperature of 230° C. and under a vacuum of $10^{-3}$ mmHg. The yield of distillate for this operation is 9.9%.

This distillate is then heated at 85° C. for 48 hours, under a continuous stream of nitrogen, in a glass reactor equipped with a mechanical stirrer.

The oil obtained is saponified for 4 hours at reflux, in the presence of 175 g of 50% potassium hydroxide and 875 g of ethanol, in a glass reactor equipped with a mechanical stirrer and on which is mounted a condenser. At the end of the reaction, the mixture is cooled to 30° C. and then diluted by adding demineralized water. The aqueous-alcoholic solution (AAS) obtained is then extracted with 1,2-dichloroethane using a separating funnel.

The organic phases are then combined and dried over anhydrous sodium sulphate. The dissolved unsaponifiable fraction is finally recovered after evaporating off the solvent and drying under vacuum. This step is carried out in a rotary evaporator, at 70° C., under a vacuum of 1 mmHg for 2 hours. 163 g of unsaponifiable fraction from avocado are thus recovered, and are then stored under nitrogen while awaiting analysis. The physicochemical and chromatographic analysis of this fraction gave the following results:
peroxide value: 26.3 meq $O_2$/kg
saponification number: 10.7 mg KOH/g
incineration residue: 0.3%
furan lipid content: 62.2%
fatty alcohol content: 14.1
heavy compounds: 13.2%

Intermediate Conclusions

TABLE 1

Comparison of the various processes for obtaining the unsaponifiable fraction from avocado/Influence of the nature of the heat treatment

| Example | Variant (1) | Gain in yield (%) (1) | Furan lipids (%) (2) | Heavy compounds (%) | Peroxide value (meq $O_2$/kg) |
|---|---|---|---|---|---|
| 1 | Vigorous heating of the fruit | — | 49.2 | 22.3 | 87.2 |
| 2 | Vigorous heating of the oil | +12% | 57.6 | 14.3 | 23.2 |
| 3 | Vigorous heating of the distillate | +29% | 62.2 | 13.2 | 26.3 |

(1) Gain relative to Example 1 chosen as the reference process
(2) Furan lipid content of the unsaponifiable fraction obtained The standard process of vigorous heating of the fruit (Example 1) gives a highly oxidized product (Ip=87.2 meq $O_2$/kg) and has an appreciable content of heavy compounds (22.3%), these compounds being derived from chemical condensation processes, activated by the temperature and the long duration of the process.

The process of vigorous heating of the oil, carried out under inert atmosphere, allows an appreciable gain in yield (+12% relative to the reference process of heating of the fruit). It also leads to a product that is less oxidized (peroxide value<30), with a lower content of heavy compounds (about 14% as opposed to 22% previously) and, conversely, is richer in furan lipids (57% as opposed to 49%).

The process of heating of the distillate itself offers a better yield (+29%) and a high content of furan lipids in the final unsaponifiable material (62%). Consequently, the overall yield of furan lipids is thus greatly increased.

EXAMPLE 4

Process of Vigorous Heat Treatment of the Distillate in the Presence of a Catalyst 50 kg of fresh avocados are cut into thin slices 2 to 5 mm thick, including the kernel, using a disc slicer. The drying device is a temperature-regulated oven with a stream of hot air. The sliced avocados are spread to a thickness of 4 to 5 cm onto staged trays. The drying temperature is set at 70° C. and its duration is 48 hours. Once dried, the fruit is ground and then subjected to a cold pressing. This operation is performed on a small laboratory Komet press. The extracted oil is then filtered through a Büchner funnel, and then stored under nitrogen protected from light and moisture.

The oil obtained is then distilled in a Leybold KDL 4 wiped-film molecular distillation device, at a temperature of 230° C. and under a vacuum of $10^{-3}$ mmHg. The yield of distillate for this operation is 9.9%.

This distillate is then heated at 85° C. for 2 hours in the presence of 5% acidic alumina (catalyst), under a continuous stream of nitrogen, and in a glass reactor equipped with a mechanical stirrer.

The heat-treated distillate is filtered and saponified for 4 hours at reflux, in the presence of 175 g of 50% potassium hydroxide and 875 g of ethanol, in a glass reactor equipped with a mechanical stirrer and on which is mounted a condenser. At the end of the reaction, the mixture is cooled to 30° C. and then diluted by adding demineralized water. The aqueous-alcoholic solution (AAS) obtained is then extracted with 1,2-dichloroethane using a separating funnel.

The organic phases are then combined and dried over anhydrous sodium sulphate. The dissolved unsaponifiable fraction is finally recovered after evaporating off the solvent and drying under vacuum. This step is carried out in a rotary evaporator, at 70° C., under a vacuum of 1 mmHg for 2 hours. 126 g of unsaponifiable fraction from avocado are thus recovered, and are then stored under nitrogen while awaiting analysis.

The physicochemical and chromatographic analysis of this fraction gave the following results:
peroxide value: 23.3 meq $O_2$/kg
saponification number: 11.3 mg KOH/g
incineration residue: 0.2%
furan lipid content: 71.5%
fatty alcohol content: 13.9
heavy compounds: 5.2%

EXAMPLE 5

Process for the Vigorous Heat Treatment of the Distillate in the Absence of Catalyst 50 kg of fresh avocados are cut into thin slices 2 to 5 mm thick, including the kernel, using a disc slicer. The drying device is a temperature-regulated oven with a stream of hot air. The sliced avocados are spread to a thickness of 4 to 5 cm onto staged trays. The drying temperature is set at 70° C. and its duration is 48 hours. Once dried, the fruits are ground and then subjected to a cold pressing. This operation is performed on a small laboratory Komet press. The extracted oil is then filtered through a Büchner funnel, and then stored under nitrogen protected from light and moisture.

The oil obtained is then distilled in a Leybold KDL 4 wiped-film molecular distillation device, at a temperature of 230° C. and under a vacuum of $10^{-3}$ mmHg. The yield of distillate for this operation is 9.9%.

This distillate is then heated at 85° C. for 2 hours, under a continuous stream of nitrogen, and in a glass reactor equipped with a mechanical stirrer.

The heat-treated distillate is saponified for 4 hours at reflux, in the presence of 175 g of 50% potassium hydroxide and 875 g of ethanol, in a glass reactor equipped with a mechanical stirrer and on which is mounted a condenser. At the end of the reaction, the mixture is cooled to 30° C. and then diluted by adding demineralized water. The aqueous-alcoholic solution (AAS) obtained is then extracted with 1,2-dichloroethane using a separating funnel.

The organic phases are then combined and dried over anhydrous sodium sulphate. The dissolved unsaponifiable fraction is finally recovered after evaporating off the solvent and drying under vacuum. This step is carried out in a rotary evaporator, at 70° C., under a vacuum of 1 mmHg for 2 hours. 17 g of unsaponifiable fraction from avocado are thus recovered, and are then stored under nitrogen while awaiting analysis.

The physicochemical and chromatographic analysis of this fraction gave the following results:
peroxide value: 21.2 meq $O_2$/kg
saponification number: 10.1 mg KOH/g
incineration residue: 0.1%
furan lipid content: 70.1%
fatty alcohol content: 14.2%
heavy compounds: 3.2%

CONCLUSION

The addition of an alumina catalyst drastically increases the rate of conversion since, after 2 hours of heat treatment, 126 g of unsaponifiable material are obtained, as opposed to only 17 g in the absence of alumina.

COUNTER EXAMPLE

Process Without Vigorous Heat Treatment of the Fruit or its Optionally Concentrated Oil 50 kg of fresh avocados are cut into thin slices 2 to 5 mm thick, including the kernel, using a disc slicer. The drying device is a heat-regulated oven with a stream of hot air. The sliced avocados are spread to a thickness of 4 to 5 cm onto staged trays. The drying temperature is set at 65° C., and its duration is 72 hours. Once dried, the fruits are ground and then subjected to a cold pressing. This operation is performed on a small laboratory Komet press. The extracted oil is then filtered through a Büchner funnel and then stored under nitrogen protected from light and moisture.

The oil obtained is then distilled in a Leybold KDL 4 wiped-film molecular distillation device, at a temperature of 230° C. and under a vacuum of $10^{-3}$ mmHg. The yield of distillate for this operation is 9.1%.

The distillate obtained is saponified for 4 hours at reflux, in the presence of 175 g of 50% potassium hydroxide and 875 g of ethanol, in a glass reactor equipped with a mechanical stirrer and on which is mounted a condenser. At the end of the reaction, the mixture is cooled to 30° C. and then diluted by adding demineralized water. The aqueous-alcoholic solution (AAS) obtained is then extracted with 1,2-dichloroethane using a separating funnel.

The organic phases are then combined and dried over anhydrous sodium sulphate. The dissolved unsaponifiable fraction is finally recovered after evaporating off the solvent under vacuum at low temperature. This step is carried out in a rotary evaporator, at 70° C., under a vacuum of 1 mmHg, for 2 hours. 105 g of unsaponifiable fraction from avocado are thus recovered, and are then stored under nitrogen while awaiting analysis.

The physicochemical and chromatographic analysis of this fraction gave the following results:
- peroxide value: 5.1 meq $O_2$/kg
- saponification number: 11.3 mg KOH/g
- incineration residue: 0.4%
- furan lipid content: 5.2%
- fatty alcohol content: 13.7
- heavy compounds: 31.2%

CONCLUSION

In the absence of a step of vigorous heating of the fruit or of the oil which would result from unheated fruit, the furan lipid content of the unsaponifiable fraction from avocado obtained is extremely low (substantially less than 10%).

The invention claimed is:

1. A process for obtaining a furan lipid-rich unsaponifiable material from avocado, comprising:
   (I) controllably dehydrating a fresh avocado fruit or an avocado fruit that has undergone a preliminary transformation, wherein the dehydrating is performed at a temperature between −50° C. and 75° C.,
   (II) extracting oil from the dehydrated fruit,
   (III) alternatively,
      a. heat treating the extracted oil at a temperature from 80 to 150° C., and then concentrating the unsaponifiable fraction of the oil, or
      b. concentrating the unsaponifiable fraction of the oil, followed by heat treating at a temperature from 80 to 150° C., followed by
   (IV) saponificating and extracting of the unsaponifiable material.

2. The process for obtaining a furan lipid-rich unsaponifiable material from avocado according to claim 1, wherein the step of heat treating in (III)(a) or (III)(b) is carried out in the presence of a catalyst.

3. The process for obtaining a furan lipid-rich unsaponifiable material from avocado according to claim 2, wherein the catalyst is an acid catalyst of homogenous mineral or organic catalyst, chosen from the group of hydrochloric acid, sulphuric acid, acetic acid and para-toluenesulphonic acid, or a heterogeneous solid catalyst chosen from the group consisting of silica, alumina, silica-aluminas, zirconias, zeolites and acidic resins.

4. The process for obtaining a furan lipid-rich unsaponifiable material from avocado according to claim 3, wherein the catalyst is of acidic alumina type, with a specific surface area at least equal to 200 $m^2$/g.

5. The process for obtaining a furan lipid-rich unsaponifiable material from avocado according to claim 1, wherein the dehydrating is selected from the group consisting of drying under a stream of hot air at a temperature of between 70 and 75° C. or under a controlled atmosphere, drying at atmospheric pressure or under vacuum, microwave drying, spray-drying, freeze-drying and osmotic dehydration in solution or in solid phase.

6. The process for obtaining a furan lipid-rich unsaponifiable material from avocado according to claim 5, wherein the dehydrating comprises drying in ventilated dryers, in a thin layer and under a stream of hot air, at a temperature of between 70 and 75° C. for 8 to 36 hours.

7. The process for obtaining a furan lipid-rich unsaponifiable material from avocado according to claim 1, wherein the step of extracting in (II) is carried out by a simple cold pressing or by the means of a solvent at low temperature.

8. The process for obtaining a furan lipid- rich unsaponifiable material from avocado according to claim 1, wherein the step of concentrating in (III)(a) or (III)(b) is a cold crystallization or a molecular distillation.

9. The process for obtaining a furan lipid-rich unsaponifiable material from avocado according to claim 1, wherein the step of concentrating in III(a) or III(b) is the molecular distillation and the molecular distillation is carried out in a device selected from the group consisting of molecular distillation devices of centrifugal type and molecular devices of wiped-film type.

10. The process for obtaining a furan lipid-rich unsaponifiable material from avocado according to claim 1, wherein the saponification step of (IV) is carried out in the presence of potassium hydroxide or sodium hydroxide in an alcoholic medium, followed by one or more extractions.

11. The process for obtaining a furan lipid-rich unsaponifiable material from avocado according to claim 10, wherein the extraction takes place by liquid-liquid extraction with an organic solvent chosen from the group consisting of alkanes, haloalkanes, aromatic solvents and ethers.

12. The process for obtaining a furan lipid-rich unsaponifiable material from avocado according to claim 10, wherein the organic solvent for the extraction is 1,2-dichloroethane.

13. The process for obtaining a furan lipid-rich. unsaponifiable material from avocado according to claim 1, further comprising a deodorization step.

* * * * *